US010726741B2

(12) United States Patent
Savitsky et al.

(10) Patent No.: US 10,726,741 B2
(45) Date of Patent: Jul. 28, 2020

(54) SYSTEM AND METHOD FOR CONVERTING HANDHELD DIAGNOSTIC ULTRASOUND SYSTEMS INTO ULTRASOUND TRAINING SYSTEMS

(71) Applicants: Eric Savitsky, Santa Monica, CA (US); Gabriele Nataneli, Beverly Hills, CA (US)

(72) Inventors: Eric Savitsky, Santa Monica, CA (US); Gabriele Nataneli, Beverly Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1037 days.

(21) Appl. No.: 15/198,994

(22) Filed: Jun. 30, 2016

(65) Prior Publication Data

US 2016/0314715 A1      Oct. 27, 2016

Related U.S. Application Data

(63) Continuation-in-part of application No. 13/481,725, filed on May 25, 2012, now Pat. No. 10,026,338, which is a continuation-in-part of application No. 13/243,758, filed on Sep. 23, 2011, now Pat. No. 8,480,404, which is a continuation of application No. 11/720,515, filed as application No. PCT/US2005/043155 on Nov. 30, 2005, now abandoned.

(60) Provisional application No. 60/631,488, filed on Nov. 30, 2004, provisional application No. 61/491,126, filed on May 27, 2011, provisional application No. 61/491,131, filed on May 27, 2011, provisional application No. 61/491,134, filed on May 27, 2011, (Continued)

(51) Int. Cl.
*G09B 23/28* (2006.01)
*A61B 8/00* (2006.01)

(52) U.S. Cl.
CPC .......... *G09B 23/286* (2013.01); *A61B 8/4254* (2013.01); *A61B 8/4427* (2013.01); *A61B 8/4455* (2013.01); *A61B 8/461* (2013.01)

(58) Field of Classification Search
CPC .... G16H 50/50; A61B 8/4254; A61B 8/4444; A61B 8/4472; A61B 8/54; A61B 8/58; A61B 8/44; A61B 8/4209; A61B 8/4281; G01S 7/5208; G01S 7/52096; G09B 23/28; G09B 23/30
See application file for complete search history.

(56) References Cited

U.S. PATENT DOCUMENTS 5,609,485 A    3/1997 Bergman et al.
5,701,900 A   12/1997 Shehada et al.
(Continued)

FOREIGN PATENT DOCUMENTS

WO    WO-2011091613 A1 *  8/2011    ........... A61B 8/4254

*Primary Examiner* — Angela M Hoffa
*Assistant Examiner* — Helene Bor
(74) *Attorney, Agent, or Firm* — Cislo & Thomas, LLP (57) ABSTRACT

A system and method for converting a commercial diagnostic ultrasound transducer into a medical training device that is used for simulated ultrasound training; or a system and method for adding a training option to a standard ultrasound diagnostic system by attaching a motion sensor accessory to the commercial diagnostic ultrasound transducer.

9 Claims, 11 Drawing Sheets

Related U.S. Application Data provisional application No. 61/491,135, filed on May 27, 2011, provisional application No. 61/491,138, filed on May 27, 2011, provisional application No. 62/187,085, filed on Jun. 30, 2015.

(56) References Cited

U.S. PATENT DOCUMENTS

| | | | |
|---|---|---|---|
| 5,767,839 | A | 6/1998 | Rosenberg |
| 5,776,062 | A | 7/1998 | Nields |
| 5,800,350 | A | 9/1998 | Coppleson et al. |
| 6,068,597 | A | 5/2000 | Lin |
| 6,074,213 | A | 6/2000 | Hon |
| 6,117,078 | A | 9/2000 | Lysyansky et al. |
| 6,122,538 | A | 9/2000 | Sliwa et al. |
| 6,133,395 | A | 10/2000 | Miyata et al. |
| 6,156,213 | A | 12/2000 | Dudley et al. |
| 6,238,341 | B1 * | 5/2001 | Mullen ............... A61B 8/00 600/437 |
| 6,511,427 | B1 | 1/2003 | Sliwa et al. |
| 6,780,016 | B1 | 8/2004 | Toly |
| 6,896,650 | B2 | 5/2005 | Tracey et al. |
| 6,916,283 | B2 | 7/2005 | Tracey et al. |
| 7,037,258 | B2 | 5/2006 | Chatenever et al. |
| 7,371,068 | B2 | 5/2008 | Lloyd et al. |
| 7,794,388 | B2 | 9/2010 | Draxinger et al. |
| 7,850,454 | B2 | 12/2010 | Toly |
| 7,857,626 | B2 | 12/2010 | Toly |
| 2001/0031920 | A1 | 10/2001 | Kaufman et al. |
| 2002/0099310 | A1 | 7/2002 | Kimchy |
| 2002/0168618 | A1 | 11/2002 | Anderson et al. |
| 2004/0009459 | A1 | 1/2004 | Anderson et al. |
| 2004/0043368 | A1 | 3/2004 | Hsieh et al. |
| 2004/0234113 | A1 | 11/2004 | Miga |
| 2005/0119569 | A1 | 6/2005 | Ohtake |
| 2005/0181342 | A1 | 8/2005 | Toly |
| 2005/0283075 | A1 | 12/2005 | Ma et al. |
| 2007/0032726 | A1 | 2/2007 | Osaka et al. |
| 2007/0161904 | A1 * | 7/2007 | Urbano ............... A61B 8/00 600/459 |
| 2008/0009743 | A1 * | 1/2008 | Hayasaka ............ A61B 8/0833 600/461 |
| 2008/0204004 | A1 | 8/2008 | Anderson |
| 2008/0221446 | A1 * | 9/2008 | Washburn ............ A61B 8/00 600/437 |
| 2008/0269606 | A1 | 10/2008 | Matsumura |
| 2009/0275833 | A1 * | 11/2009 | Ikeda ................... A61B 8/0833 600/443 |
| 2010/0179428 | A1 * | 7/2010 | Pedersen ............. A61B 8/00 600/443 |
| 2011/0269097 | A1 | 11/2011 | Sporbert et al. |
| 2012/0238875 | A1 * | 9/2012 | Savitsky ............. A61B 8/4254 600/443 |
| 2014/0004488 | A1 * | 1/2014 | Tepper ................ A61B 8/58 434/219 |
| 2015/0056591 | A1 * | 2/2015 | Tepper ................ G06T 19/00 434/262 |

\* cited by examiner

SYSTEM AND METHOD FOR CONVERTING HANDHELD DIAGNOSTIC ULTRASOUND SYSTEMS INTO ULTRASOUND TRAINING SYSTEMS

CROSS REFERENCE TO RELATED APPLICATIONS

This patent application is a continuation-in-part and claims the benefit of U.S. patent application Ser. No. 13/481,725 filed May 25 2012, which is a continuation-in-part and claims the benefit of U.S. patent application Ser. No. 13/243,758 filed Sep. 23, 2011 for Multimodal Ultrasound Training System, which is a continuation of U.S. patent application Ser. No. 11/720,515 filed May 30, 2007 for Multimodal Medical Procedure Training System, which is the national stage entry of PCT/US05/43155, entitled "Multimodal Medical Procedure Training System" and filed Nov. 30, 2005, which claims priority to U.S. Provisional Patent Application No. 60/631,488, entitled Multimodal Emergency Medical Procedural Training Platform and filed Nov. 30, 2004; U.S. patent application Ser. No. 13/481,725 also claims the benefit of U.S. Provisional Application Ser. No. 61/491,126 filed May 27, 2011 for Data Acquisition, Reconstruction, and Simulation; U.S. Provisional Application Ser. No. 61/491,131 filed May 27, 2011 for Data Validator; U.S. Provisional Application Ser. No. 61/491,134 filed May 27, 2011 for Peripheral Probe with Six Degrees of Freedom Plus 1; U.S. Provisional Application Ser. No. 61/491,135 filed May 27, 2011 for Patient-Specific Advanced Ultrasound image Reconstruction Algorithms; and U.S. Provisional Application Ser. No. 61/491,138 filed May 27, 2011 for System and Method for Improving Acquired Ultrasound-Image Review. Each of those applications is incorporated in their entirety here by this reference.

This application also claims the benefit of U.S. Provisional Patent Application No. 62/187,085 filed Jun. 30, 2015 for System and Method for Converting Handheld Diagnostic Ultrasound Systems into Ultrasound Training Systems.

BACKGROUND

Over the past decade, several companies started commercializing compact medical devices that interface directly with smartphones and tablets or other portable computers. Of particular interest are ultrasound probes. They plug-in directly into the computing device and use its processing capabilities to display high quality diagnostic ultrasound images in real-time, rivaling traditional machinery only found at large clinical institutions. By virtue of their versatility and portability, these technologies carry profound benefits for critical care. However, one major obstacle remains. Mastering how to use an ultrasound transducer to diagnose a patient requires extensive training and hands-on experience. This invention introduces a new hardware accessory that allows using the same system for both clinical applications and self-directed training through simulation.

SUMMARY OF THE INVENTION

The invention of the present application is directed towards a method and system for allowing a motion sensor to be combined with an ultrasound transducer probe and to communicate with a mobile device to allow a real ultrasound transducer probe to also be converted into a training tool. The system comprises a motion sensor encased in a housing to function as a motion sensor accessory to an ultrasound transducer probe (hereinafter "probe" or "ultrasound probe"). The motion sensor accessory can be attached and removed from the probe or could be permanently affixed to its exterior or interior. When the motion sensor accessory is attached to the probe and turned on, the probe is used as a training tool. When the motion sensor accessory is removed from the probe or turned off, the probe can be used as an actual ultrasound tool on real patients for actual diagnosis of a medical condition. The motion sensor accessory may be supplemented with a carrier configured for affixing the motion sensor to the probe.

Software can be downloaded on to a computing device, such as a mobile phone or smartphone, a tablet, a notebook computer, a desktop computer, optical head-mounted displays, and other devices that can display images so that the motion sensor accessory can communicate with the user's computing device. The motion sensor accessory may further comprise a communication module with a wireless interface to allow the motion sensor components to communicate with the computing device wirelessly. The required hardware and software can run simulation and training programs.

The probe may be an actual ultrasound probe capable of capturing ultrasound images. If the accessory is not permanently attached and is removable, instruction materials will direct the user to firmly affix the accessory to the existing probe using the carrier. The instructions will also guide the user to download and install the software (e.g. a mobile app) on the computing device. The mobile app may use a graphical user interface (GUI) to instruct the user on how to establish communication with the motion sensor accessory and use the system to learn how to operate an ultrasound probe with the provided simulation.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to he encompassed within the spirit and scope of the invention.

With reference to FIGS. 1-4, the ultrasound system 100 includes an ultrasound go machine 102 and an ultrasound probe 104. The ultrasound machine 102 displays an ultrasound image 106. In a version of the invention, the image displayed by the ultrasound machine 102 includes a probe indicator icon 108. In another embodiment, the ultrasound probe 104 also includes a reference indicator 110, which is a direction indicator to orient the ultrasound probe 104. The ultrasound machine 102 can be any computing device that can receive input from an ultrasound probe 104, process the inputted data from the ultrasound probe 104, and display ultrasound images based on the inputted data. In the preferred embodiment, the ultrasound machine 102 is a mobile device, such as a smartphone, tablet, notebook, and head-mounted displays, including virtual reality headsets, augmented reality devices, and other wearable technologies. Computing devices, and some mobile device, may also include projection technologies, holographic displays, light field displays, and the like.

The ultrasound probe 104 communicates with the ultrasound machine 102. In a version of the invention, the ultrasound probe 104 communicates with the ultrasound machine 102 through a data cable 112. In other versions, the communication may be wireless.

The ultrasound probe 104 includes an ultrasound transducer 114, ultrasound circuitry 116, a motion sensor 118 (e.g. a motion sensor that can detect orientation and position, and a probe housing 120. When the accessory is affixed permanently, the probe housing 120 encases the ultrasound transducer 114 and the motion sensor 118.

The ultrasound transducer 114 transmits acoustic waves 122 and measures the reflected acoustic waves 122 to produce a reflected wave signal 124. The ultrasound circuitry 116 receives the reflected wave signal 124 from the ultrasound transducer 114 and transmits an image signal 126 to the ultrasound machine 102. The motion sensor 118 measures the position and orientation of the ultrasound probe 104.

Preferably, the motion sensor 118 is an inertial sensor. In some embodiments, the motion sensor 118 includes an accelerometer 130, a gyroscope 132, and a magnetometer 134. The motion sensor 118 can be used to detect misalignment and provide a visual alert (for example, in conjunction with the probe indicator icon 108) or an auditory alert to the user about the reference indicator 110 alignment.

In a version of the invention, the ultrasound probe 104 also includes a sensing head 128 at which the ultrasound transducer 114 transmits acoustic waves 122 and measures reflected waves 124.

Figure 4:
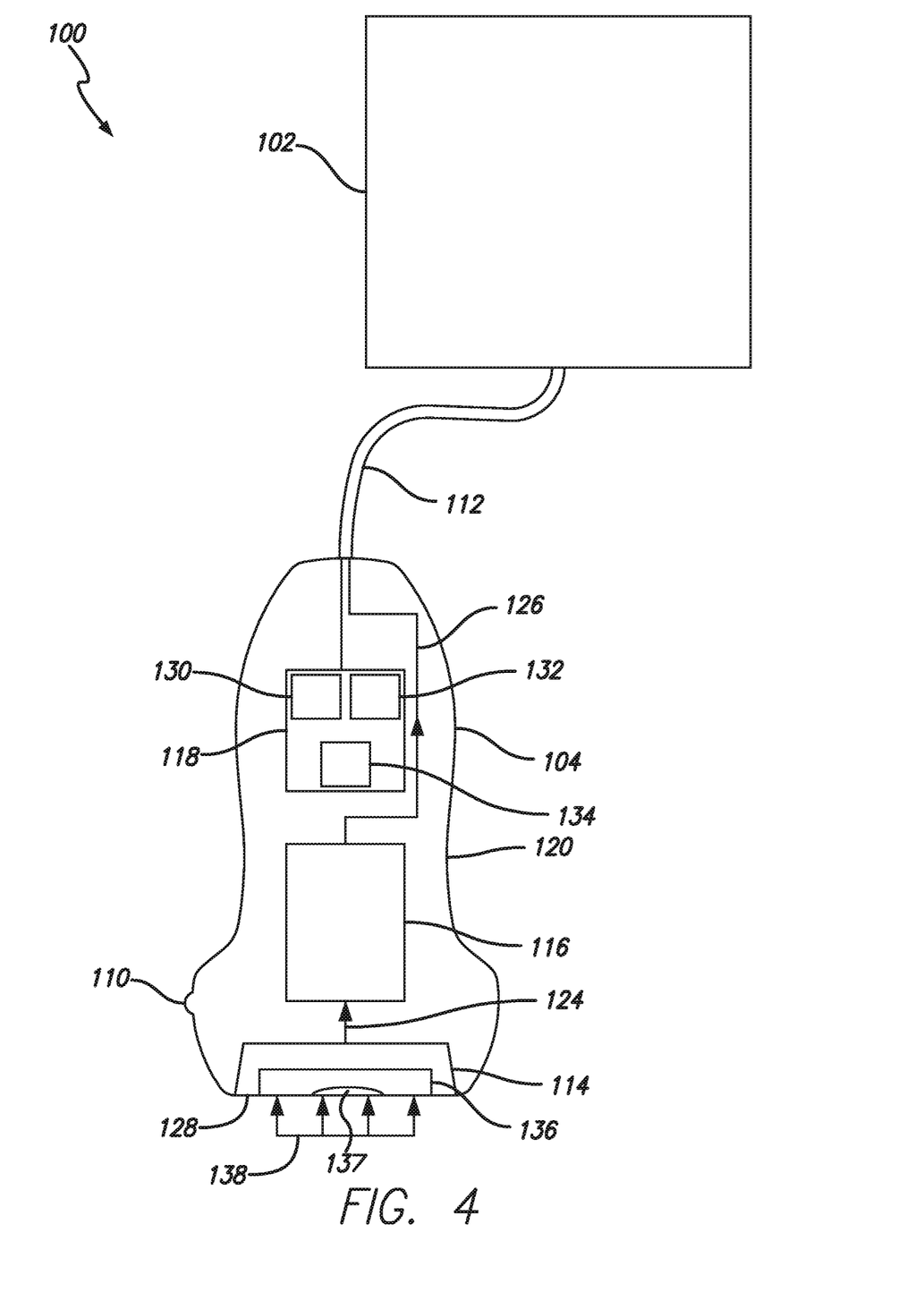
FIG. 4 is a schematic of an embodiment of the disclosed ultrasound system that includes a compression sensor.

In a preferred version, the ultrasound probe 104 also includes a compression sensor 136 that measures the force 138 applied to the sensing head 128. In that version, the probe housing 120 also encases the compression sensor 136. The compression sensor 136 allows the user to investigate the elastic properties of the underlying anatomy in the simulated environment by pressing the tip of the device (for example, the sensing head 128) against a surface with varying amounts of force 138. Preferably, the compression sensor 136 is a resistive strain gauge or other mechanical means that will not interfere with the operation of the ultrasound transducer 114. If the compression sensor 136 interferes with the operation of the ultrasound transducer 114, in some versions the compression sensor 136 may be disabled mechanically when the ultrasound system 100 is operated in the standard mode. In an alternative embodiment, the ultrasound transducer 114 (which is typically built using a highly sensitive piezoelectric element) can itself be used to measure compression directly without a separate compression sensor 136. Other types of sensors can also be employed by the ultrasound probe 104, such as a temperature sensor 137.

Figure 1:
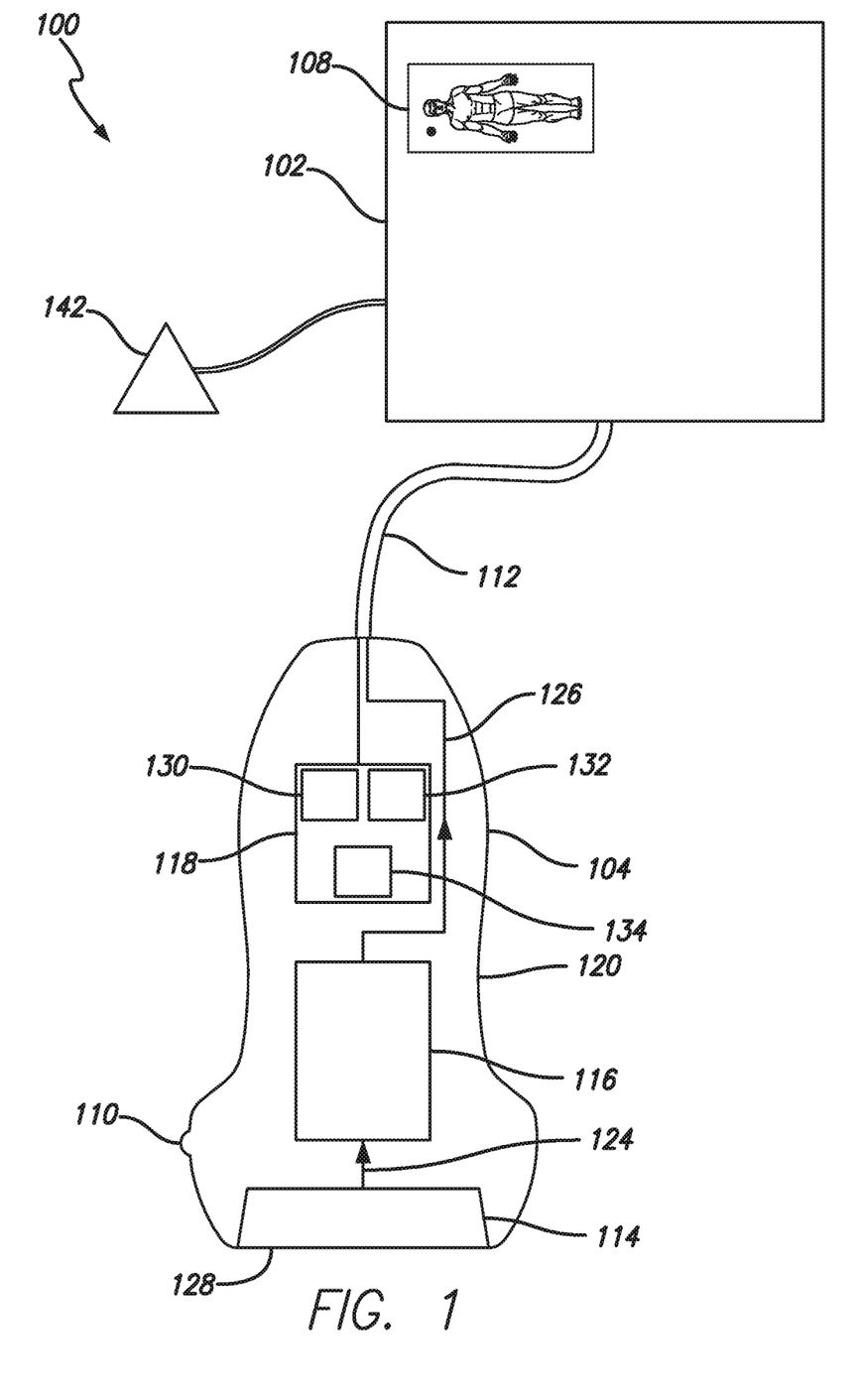
FIG. 1 is a schematic of an embodiment of the disclosed ultrasound system.
Figure 2:
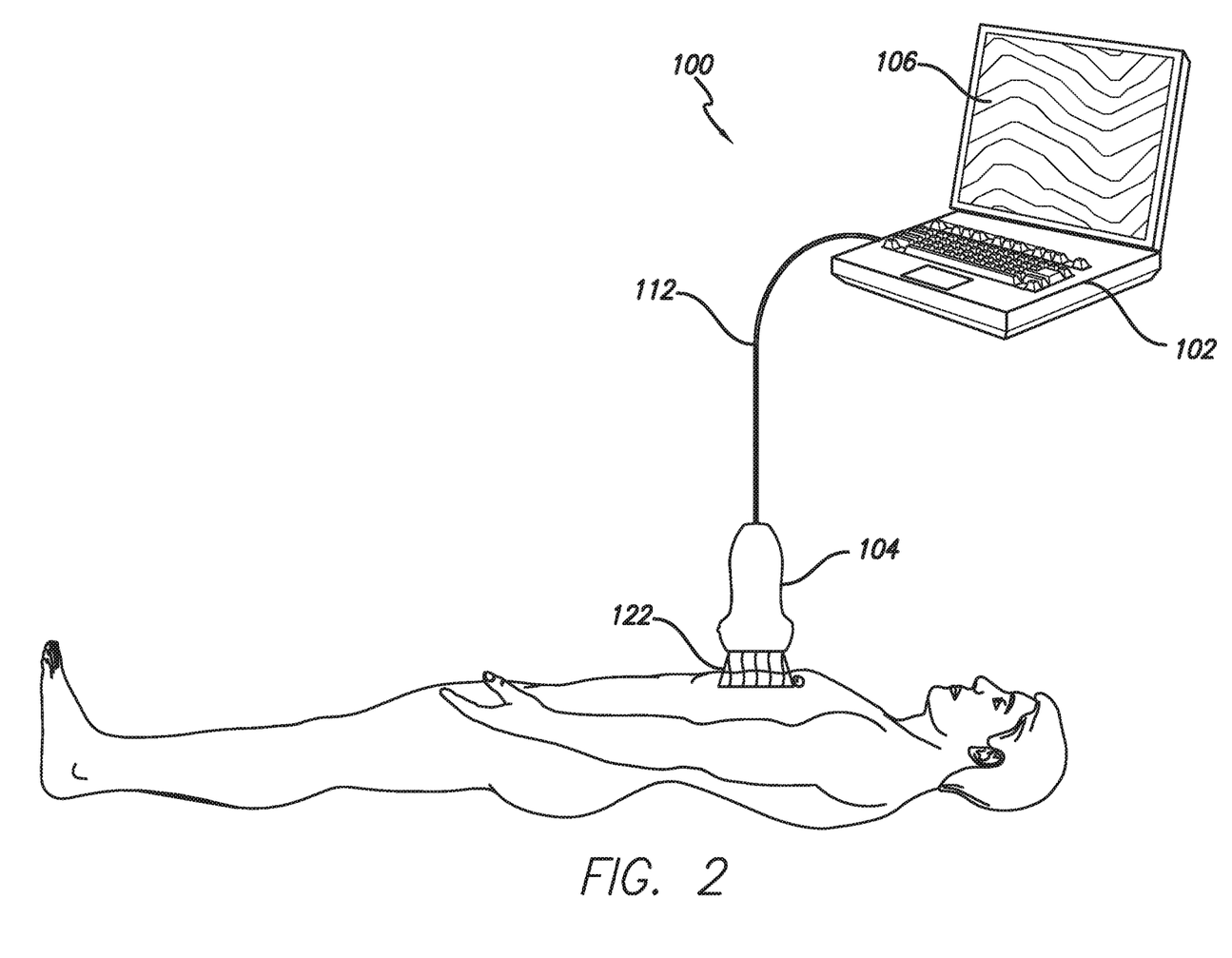
FIG. 2 is a schematic of an embodiment of the disclosed ultrasound system shown in standard mode, where the ultrasound probe is used to scan a real patient.
Figure 3:
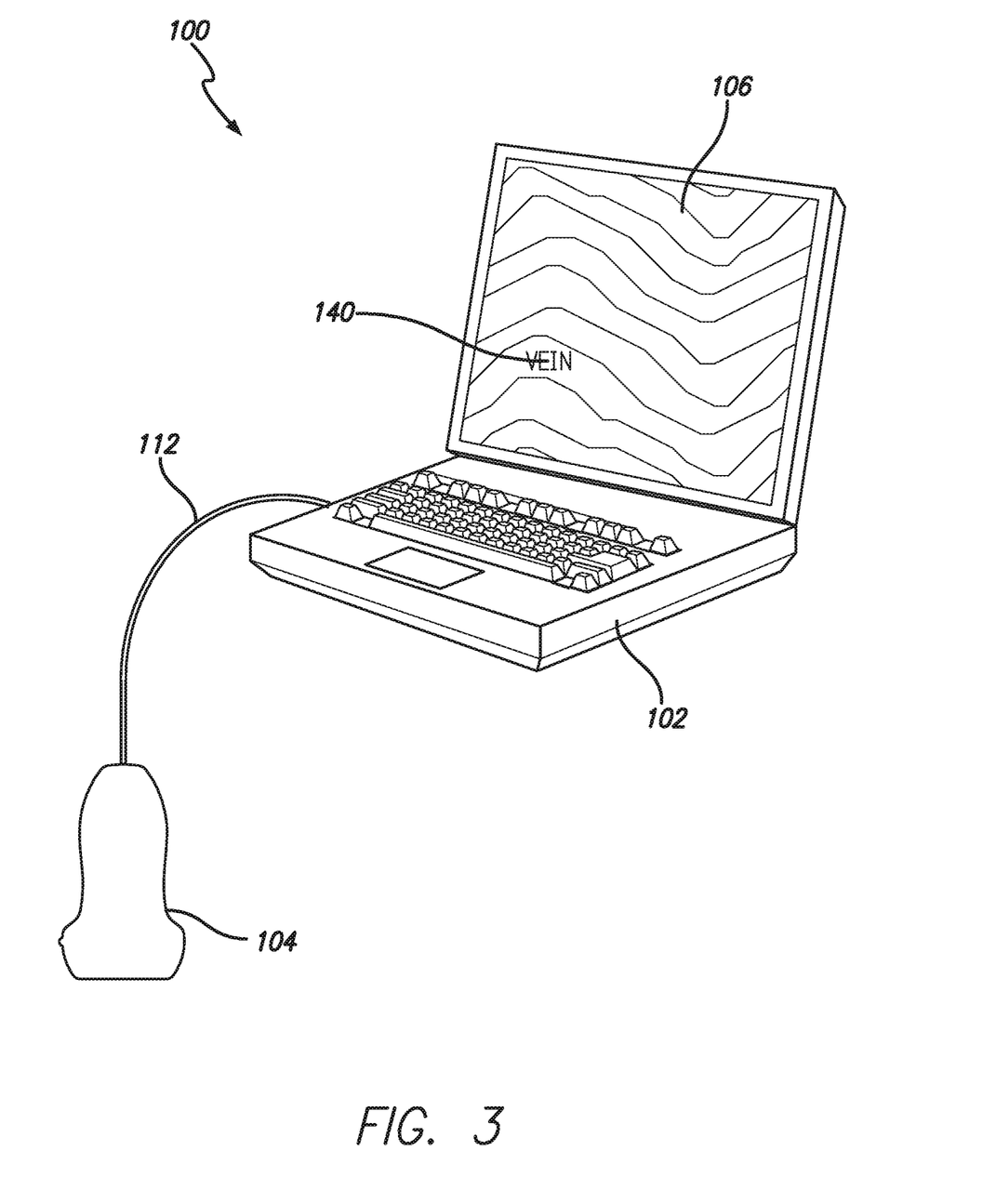
FIG. 3 is a schematic of an embodiment of the disclosed ultrasound system shown in training mode, where the same ultrasound probe as shown in FIG. 2 is now is used as a motion sensing peripheral to navigate existing patient cases.

With motion-sensing technology embedded directly within the probe housing 120, the ultrasound system 100 can operate in two separate modes: a diagnostic mode that allows the user to use the ultrasound probe 104 to scan real patients using the traditional physics of ultrasound as is done currently, and a training mode that will instead allow the user to employ the same ultrasound probe 104 as a motion sensing peripheral to navigate existing patient cases, perhaps augmented with annotations 140 that help the operator expand and refine his or her knowledge of ultrasound imaging.

More specifically, an ultrasound system 100 equipped with this novel kind of ultrasound probe 104 allows the machine to provide an additional mode of operation for training (training mode). When the training mode is enabled, the user can move the ultrasound probe 104 on the patient's body, a medical mannequin, or other arbitrary surface to navigate a pre-recorded patient case. The software loaded on the ultrasound machine 102 will respond to the motion of the ultrasound transducer 114 in a simulated environment in the same manner as when operating the ultrasound machine 102 in traditional mode (standard mode) with the real physics of ultrasound. The added benefit of the training mode is that the ultrasound operator can correlate what is observed in the real patient with a large library of prerecorded real and simulated ultrasound cases that may exhibit a wide range of known pathologies. The library of pre-recorded ultrasound cases may comprise extracted real patient ultrasound data sets (3D and 4D data), which a user can scan through using the same hand motions used by the original sonographer at the patient's bedside. The library may also provide narrated ultrasound clips (2D videos) that describe the patient findings and provide verbal and visual instruction. Furthermore, pre-recorded real and simulated ultrasound data may be augmented with additional anatomical annotations 140 that provide further insight on the details of how to use ultrasound imaging in the clinical setting. Those anatomical annotations 140 may include the labeling of pathologies or anatomical structures that are visible in the ultrasound data.

Furthermore, the disclosed solution can mitigate human error that arises from misalignment of the transducer's reference indicator 110 through manual and automatic misalignment detection.

Manual misalignment detection—The ultrasound operator can validate the appearance of a desired anatomical region with a pre-recorded case and verify that he or she oriented the ultrasound probe 104 correctly when scanning a patient. This approach does not need any additional equipment or modification beyond the disclosed embedded motion sensor.

To calibrate the system, the user places the ultrasound probe 104 at a known position with respect to the ultrasound machine 102. This is necessary to track the position of the ultrasound probe 104 with respect to the ultrasound machine 102 without the aid of any additional sensor or technology. The ultrasound machine 102 provides the user with an on-screen visual reference to establish how the sensor should be aligned (for example, with the probe indicator icon 108). All existing ultrasound machines provide such reference in the form of a small colored circle on the side of the screen. Other indicators may be used such as arrows pointing to the side the reference indicator 110 is on. For the disclosed application it also may be useful, but not necessary, to show a visual representation of the patient's body on-screen to provide additional guidance.

The ultrasound operator may then scan the patient's body, a medical mannequin, or other arbitrary surface. The motion sensor 118 informs the ultrasound machine 102 about the position of the motion sensor 118 throughout the scanning session.

Software in the ultrasound machine 102 continuously monitors the position and orientation of the ultrasound probe 104 during the scanning session using the readings from the motion sensor 118. The calibration procedure noted above allows the software to compute the relative position of the motion sensor 118 with respect to the ultrasound machine 102. If the software detects that the ultrasound probe 104 is not aligned correctly according to established medical conventions, then a visual or audio alert is generated to inform the operator about the hazard.

Automatic misalignment detection—if additional means (as explained below) are available for determining the position of the ultrasound unit with respect to the ultrasound transducer 114, software on the device can determine automatically whether or not the current orientation of the ultrasound transducer 114 is correct by checking if the expected medical conventions are being honored. This solution does not require a separate calibration step, and it may be more accurate over the extent of the scanning session.

More specifically, this approach requires two-point motion sensing solution where a reference beacon 142 is placed at a fixed position on the ultrasound machine 102 or other nearby location and the receiver is placed inside the ultrasound probe, preferably as part of the motion sensor 118. During the ultrasound scanning process, the two-point sensor solution informs the ultrasound machine 102 about the position of the motion sensor 118 relative to the ultrasound machine 102 throughout the scanning session. Software on the ultrasound machine 102 continuously monitors the position and orientation of the ultrasound probe 104 with respect to the ultrasound machine 102 during the scanning session using the readings from the two-point sensor solution (that is, the reference beacon 142 in conjunction with the motion sensor 118). If the software detects that the ultrasound probe 104 is not aligned correctly according to established medical conventions, then a visual or audio alert is generated to inform the operator about the hazard.

In some embodiments, rather than having the motion sensing technology embedded in an ultrasound probe 104, the motion sensing technology can be removably attached to the outside of the ultrasound probe 104 as shown in FIGS. 5A-6B. Therefore, the ultrasound probe 104 is essentially the same as that described above, except that the motion sensing technology has been moved to a motion sensor accessory 150 that can be removably attached to the ultrasound probe 104 as described further below.

Figure 7:
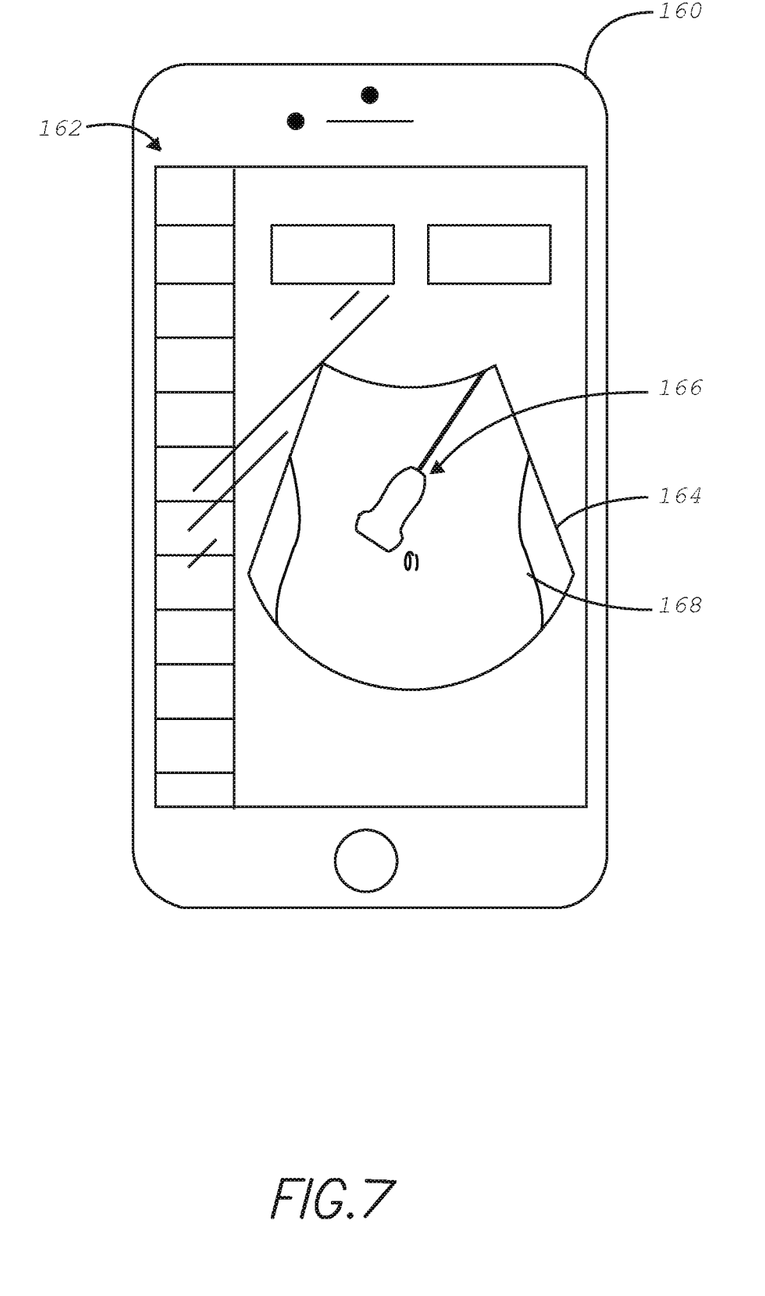
FIG. 7 shows a mobile device running an app to convert the mobile device into an ultrasound machine.
Figure 8:
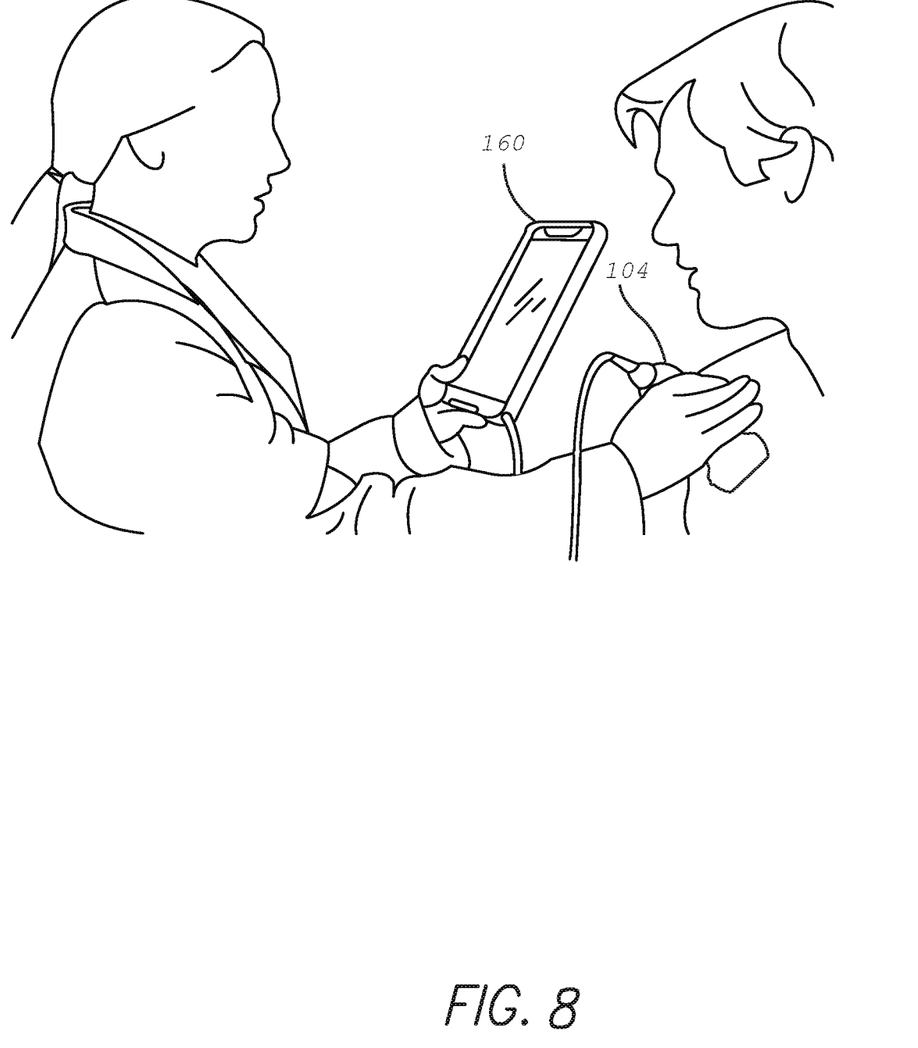
FIG. 8 shows an embodiment of the present invention in use in an actual ultrasound.
Figure 9:
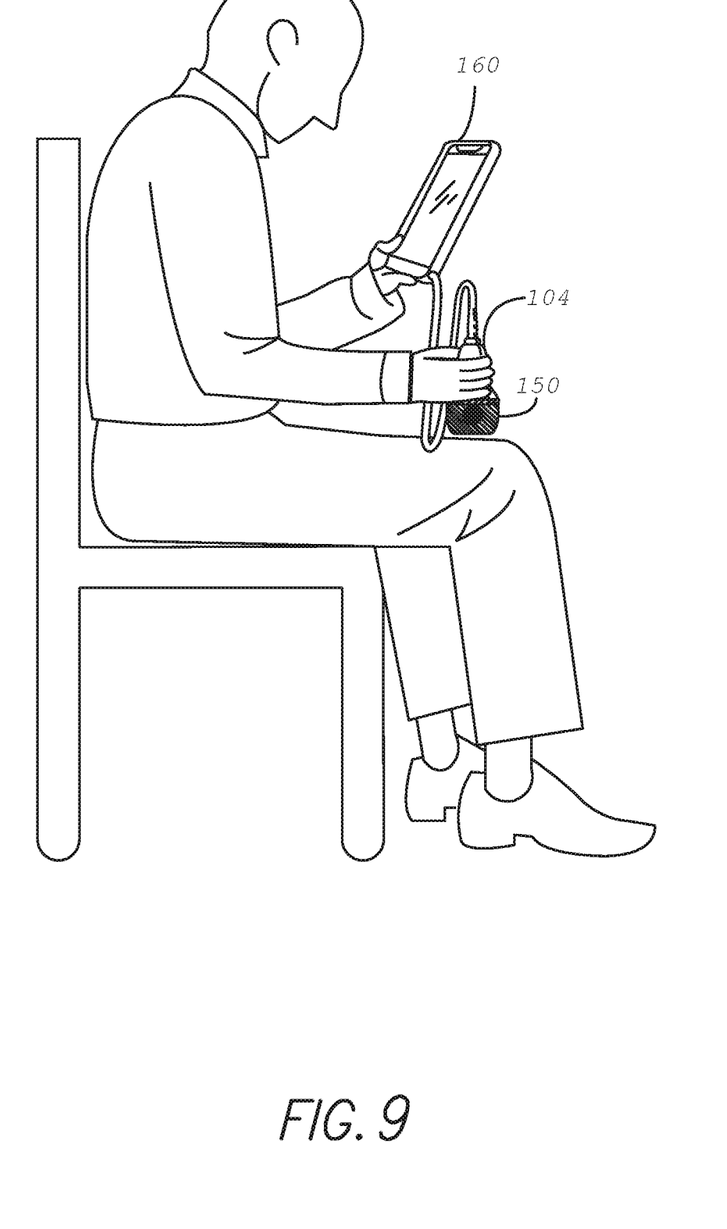
FIG. 9 shows the ultrasound probe in FIG. 8 with the motion sensor accessory attached being used as a training tool.

This allows a fully functional ultrasound probe 104 to be converted to an ultrasound training tool. Therefore, the present invention may be viewed as an ultrasound probe conversion kit for converting a commercial diagnostic ultrasound probe 104 into an ultrasound training tool. In the preferred embodiment, the kit comprises a motion sensor accessory 150 that can be attached to the ultrasound probe 104. In some embodiments, the kit may further comprise an ultrasound probe 104. In some embodiments, the kit may comprise an ultrasound machine 102. In some embodiments, the kit may comprise software or instructions to obtain software that can be loaded on to a commercially available computing device 160, and preferably, a mobile device, such as a smartphone, tablet, notebook computer, virtual reality devices, augmented reality devices, wearable devices, light field display devices, and the like, to run the software and convert the computing device 160 into an ultrasound machine 102 as shown in FIG. 7. Then, if the user wants to use the ultrasound probe 104 to conduct an actual ultrasound on a real patient, the user can remove the motion sensor accessory 150 and use the ultrasound probe on an actual patient as shown in FIG. 8. If the user wants to practice his or her technique, the user can attach the motion sensor accessory 150 on the same ultrasound probe 104 that was used on the real patient, and use the same ultrasound probe 104 as a training tool as shown in FIG. 9. Motion Sensor Several off-the-shelf solutions have delivered effective training simulators for ultrasound using only three degrees of freedom (3-DOF) motion sensors. Therefore, the preferred embodiment for the motion sensor 118 is a low-cost Inertial Measurement Unit (IMU) comprising a MEMS 3-axis accelerometer 130, 3-axis gyroscope 132, and 3-axis magnetometer 134. Care must be taken to choose components that provide a high-degree of accuracy to minimize the incidence of drift in the estimated orientation of the device. Practitioners may, however, envision other means of measuring the 3D orientation (3-DOF) and position (6-DOF) of the device using electrical, optical, electromagnetic, purely mechanical, or chemical operating principles that are consistent with the spirit of this invention. The only hard requirement is a motion sensor 118 that is miniaturized and portable enough to meet the form factor of the ultrasound probe 104, The motion sensor can employ multiple degrees of freedom (DOF), such as 2-DOF, 3-DOF, 4-DOF, 5-DOF, 6-DOF, 7-DOF, 8-DOF, 9-DOF, or 10-DOF, 11-DOF. The differentiation between the number of DOF is often an artifact of marketing rather than being based on true technical merit. For instance, a pure orientation sensor may be referred to as having 3-DOF, where each DOF determines minimum number of 3D axes in space required to describe the motion of the device, 6-DOF (where each DOF refers to each axis of a 3-axis accelerometer and 3-axis gyro), 9-DOF (where each DOF refers to each axis of a 3 axis accelerometer, 3-axis gyro, and 3-axis magnetometer), 10-DOF (where each DOF refers to each axis of a 3 axis accelerometer, 3-axis gyro, 3-axis magnetometer, and additional temperature sensor), 11-DOF (where each DOF refers to each axis of a 3 axis accelerometer, 3-axis gyro, 3-axis magnetometer, temperature sensor, and altimeter).

The preferred embodiment encompasses the following cases directly: 3-DOF (pure orientation sensing in 3D), 5-DOF (2 axes of position sensing and 3 axes of orientation sensing), and 6-DOF (3-axes of position sensing and 3 axes of orientation sensing).

Motherboard and Other Electronics

Figure 10:
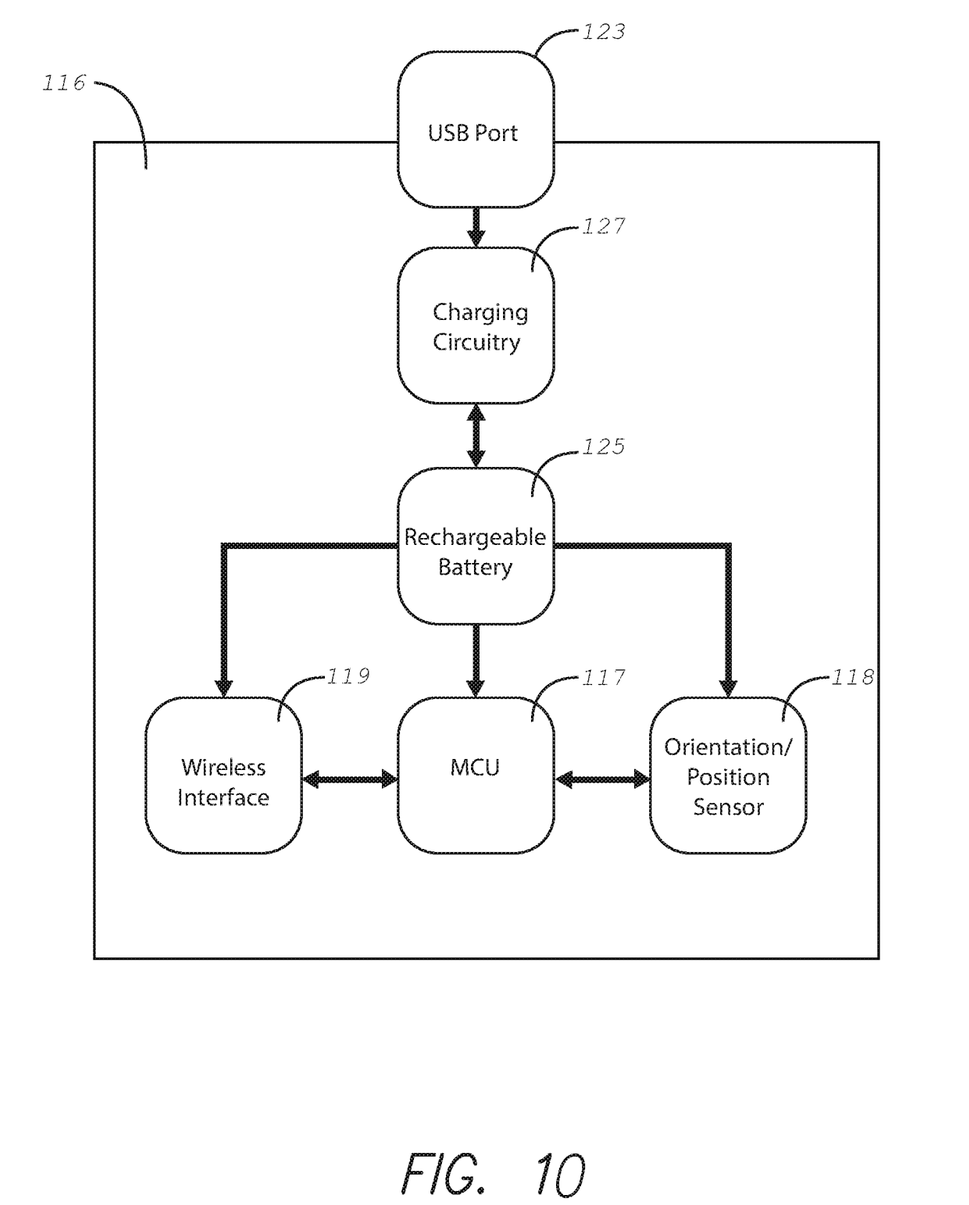
FIG. 10 shows a high level diagram of the electronic components of the attachable motion sensor accessory.

With reference to FIG. 10, in the preferred embodiments, the components of the IMU are laid out on a Printed-Circuit-Board (PCB) 116 that hosts all the required electronics to power and drive the sensors. The PCB 116 will also host a microcontroller unit (MCU) 117 to gather readings from the sensors, process the data, and deliver estimates of orientation to the interface components. Since the device is designed to work wirelessly, the sensor fusion algorithm required to transform the individual readings of the motion sensor to values of 3D orientation must on the MCU 117 and cannot be deferred to the processing unit on the paired computing device 160. Alternatively, there are commercially available single-chip IMU solutions that integrate a Digital Processing Unit (DSP) directly on the silicon and can perform all the required computations on raw sensor data internally. The choice of a single-chip IMU, relieves the MCU 117 from performing additional processing on the sensor data, allowing for cheaper components and easier integration.

Communication Interface

Since the mobile ultrasound transducer probe 104 is expected to have a direct wired connection via a data cable 112, such as USB, thunderbolt, FireWire, Ethernet, and the like, with the computing device 160, it is important that the motion sensor accessory 150 uses a wireless communication interface 119 to minimize the encumbrance of additional wires. Many low-cost and standardized solutions exist for this purpose and the most widely used standard is Bluetooth or Bluetooth Low Energy. Bluetooth is a highly desirable solution for the preferred embodiment as the large majority of mobile devices and portable computers already incorporate the hardware and software to communicate with an external Bluetooth device. Alternatively a Wi-Fi controller or other custom wireless protocol can be used for the same purpose. The wireless communication interface 119 must be mounted on the main PCB 116 along with the other components.

Battery and Charging

A wireless device needs a source of power to operate and designers may choose among a variety of battery solutions for this purpose. While single-use alkaline batteries may be adequate for this invention, a more desirable solution for the preferred embodiment is to use a form of rechargeable battery 125, which removes the need of disassembling the device for replacement and allows for a higher degree of integration to make the device smaller. The most common form of high-efficiency batteries used in wireless devices are Lithium Ion batteries or Lithium-Ion Polymer batteries. If a rechargeable battery is used, the electronics on the PCB 116 must also include recharging hardware to allow recharging the battery 125. A common solution for this purpose is to incorporate charging circuitry 127 on the PCB, for example, using a standard USB-micro port 123 on the device. Hence, the user can easily recharge the device using a widely available USB cable and a functioning USB port or USB wall-charger. Other charging circuitry 127 can be used, such as a designated power cord, wireless charging, and the like.

Carrier

As shown in FIGS. 5A-6B, the PCB 116 with all the components must be enclosed in a sturdy enclosure 151. The enclosure 151 can be manufactured using any variant of plastic or other material that can withstand wear and tear over a long period of time. The design of the enclosure 151 must warrant a small form factor and lightweight design. If the entire assembly of the motion sensor accessory 150 is too heavy it can burden the mobile ultrasound probe 104 it is attached to, and encumber its use by shifting its center of gravity away from the main axis of symmetry.

Figure 5A:
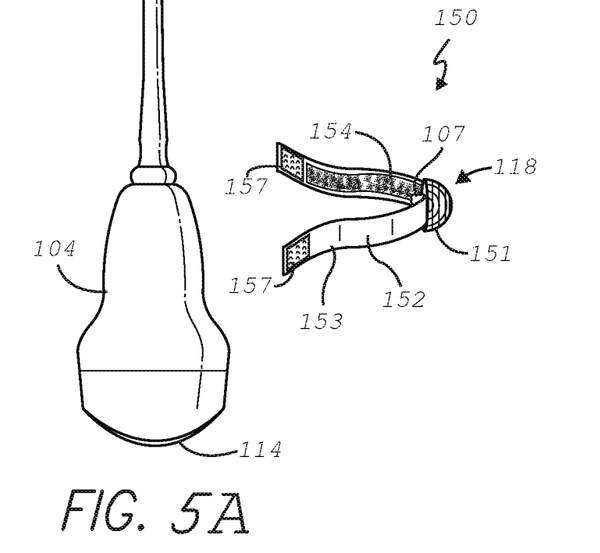
FIGS. 5A-5B show an embodiment of the present invention in which the motion sensing technology is removable from the ultrasound probe.
Figure 5B:
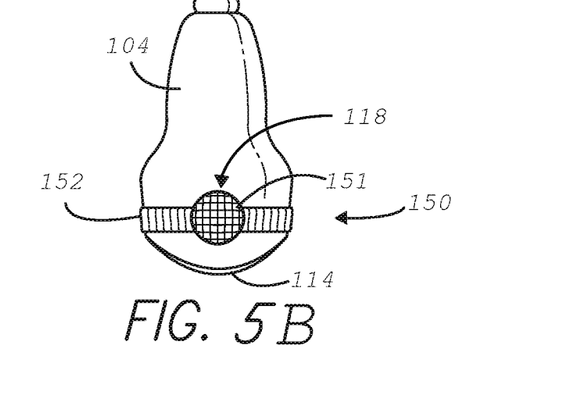

The motion sensor accessory 150 may comprise a carrier 152 that holds the enclosure 151 and attaches the enclosure 151 firmly to the exterior surface of the ultrasound probe 104. The design of the carrier 152 is challenging, because most mobile probes 104 have a curved design and they do not offer clear attachment points for external accessories. As shown in FIGS. 5A and 5B, in a first embodiment the carrier 152 may have a harness with an adjustable strap 153 that can be manually tightened with fasteners 157 (e.g., hook and loop, snap buttons, hooks, clips, magnets, and the like) to provide a firm connection between the carrier 152 and the mobile probe 104. Preferably, the straps 153 are manufactured with a high-friction material 154, such as rubber type material, on the inner surface of the straps 153 that make contact with the probe 104 to prevent the motion sensor accessory 150 from moving while in use. This design does not cover or interfere with the transducer portion 114 of the mobile probe 104 and allows users to operate the device both as a diagnostic tool to scan real patients and a training tool to scan simulated cases, without needing to remove the accessory 150.

Figure 6A:
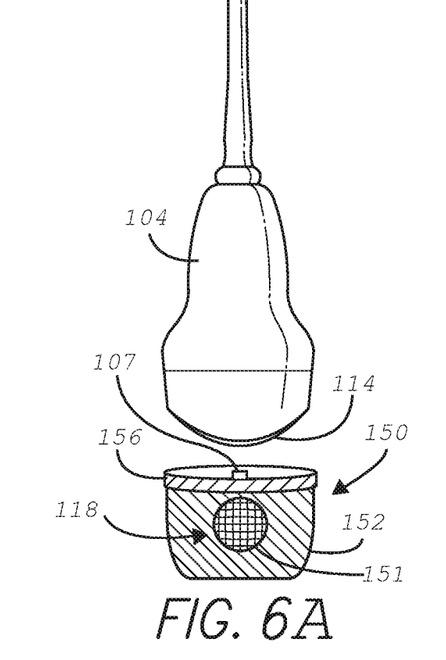
FIGS. 6A-6B show another embodiment of the present invention in which the motion sensing technology is removable from the ultrasound probe.
Figure 6B:
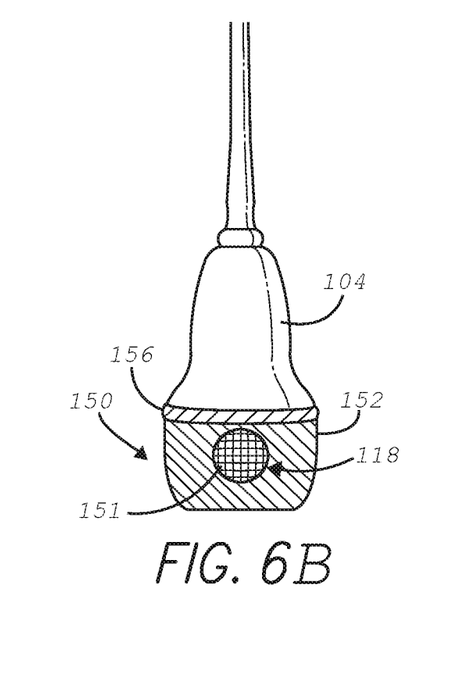

In a second embodiment, the carrier 152 is like a cap that covers the tip of the mobile probe 104 at the transducer 114 allowing the system to be used solely for training purposes while the accessory 150 is attached.

The carrier 152 can be designed to either fit a particular model of mobile ultrasound probe 104 or in a way that can accommodate a wide range of mobile ultrasound probes 104 from different vendors. In the former, the motion sensor accessory 150 can be accompanied by a multitude of different carriers 152 each designed to accommodate a specific ultrasound device available in the market. In some embodiments, the motion sensor accessory 150 may be removably attached to the carrier 152 with a fastener so that a single motion sensor accessory 150 can be used with the multitude of different carriers 152. The fastener can be a hook and loop type fastener, resistance fit fastener, screw on fastener, magnetic faster, and the like.

In some embodiments, the carrier 152 may be made of an elastic material that can be stretched to conform to the shape of the ultrasound probe 104. In some embodiments, rather than having different carriers 152, the same carrier 152 can be provided with a plurality of hollow inserts 156 that can be seated in the same carrier 152. The outer dimensions of the insert 156 may be substantially the same as the inner dimension of the carrier 152. The inner dimensions of the insert may be substantially similar to the shape of the probe 104 to which the insert was designed to fit. The insert 156 can be fastened inside the carrier 152 by resistance fit, or by other types of fasteners such as adhesives, hook and loop fasteners, high friction material, clips, magnets, and the like. The fastening mechanism should make it easy to change out the inserts 156 from the carrier 152.

In some embodiments, the motion sensor accessory 150 may comprise an accessory switch 107 for detecting whether the motion sensor accessory 150 has been attached to the ultrasound probe 104. The accessory switch 107 may be positioned on the motion sensor accessory 150 or the carrier 152 at a location where the motion sensor accessory 150 makes contact with the probe 104. For example, the switch 107 may be on the inner side of the motion sensor 118 or on the inner wall of the cap-type carrier 152. Therefore, when the motion sensor accessory 150 is attached to the ultrasound probe 104, the accessory switch 107 is automatically actuated by touching or being pressed against the ultrasound probe 104 to indicate that the motion sensor accessory 150 has been attached to the ultrasound probe 104. The accessory switch 107 may utilize a mechanical switch, such as a button, lever, slide, dial, and the like; a sensor, such as a capacitive touch sensor, a light sensor, a proximity sensor, a Hall effect sensor, or any other type of sensor that can detect when the motion sensor accessory 150 has been attached to the ultrasound probe 104; and the like, to detect whether the motion sensor accessory 150 has been attached to the probe 104.

In some embodiments, the accessory switch 107 may be located anywhere on the ultrasound probe 104 so that the user can actuate the accessory switch 107 to indicate that the motion sensor accessory 150 has been attached to the ultrasound probe 104; or the accessory switch 107 may be attached to the probe 104 at a location where attachment of the motion sensor accessory 150 automatically actuates the accessory switch 107.

In some embodiments, the accessory switch 107 may operatively be connected to the transducer 114 so as to turn the transducer 114 on and off. Therefore, when the motion sensor accessory 150 is attached to the ultrasound probe 104, the transducer 114 is automatically turned off. Conversely, when the motion sensor accessory 150 is removed from the ultrasound probe 104, the transducer 114 is automatically turned on. Alternatively, in some embodiments, the user can actuate the accessory switch 107 to turn the transducer 114 on and off.

Operating Modes

Figure 11:
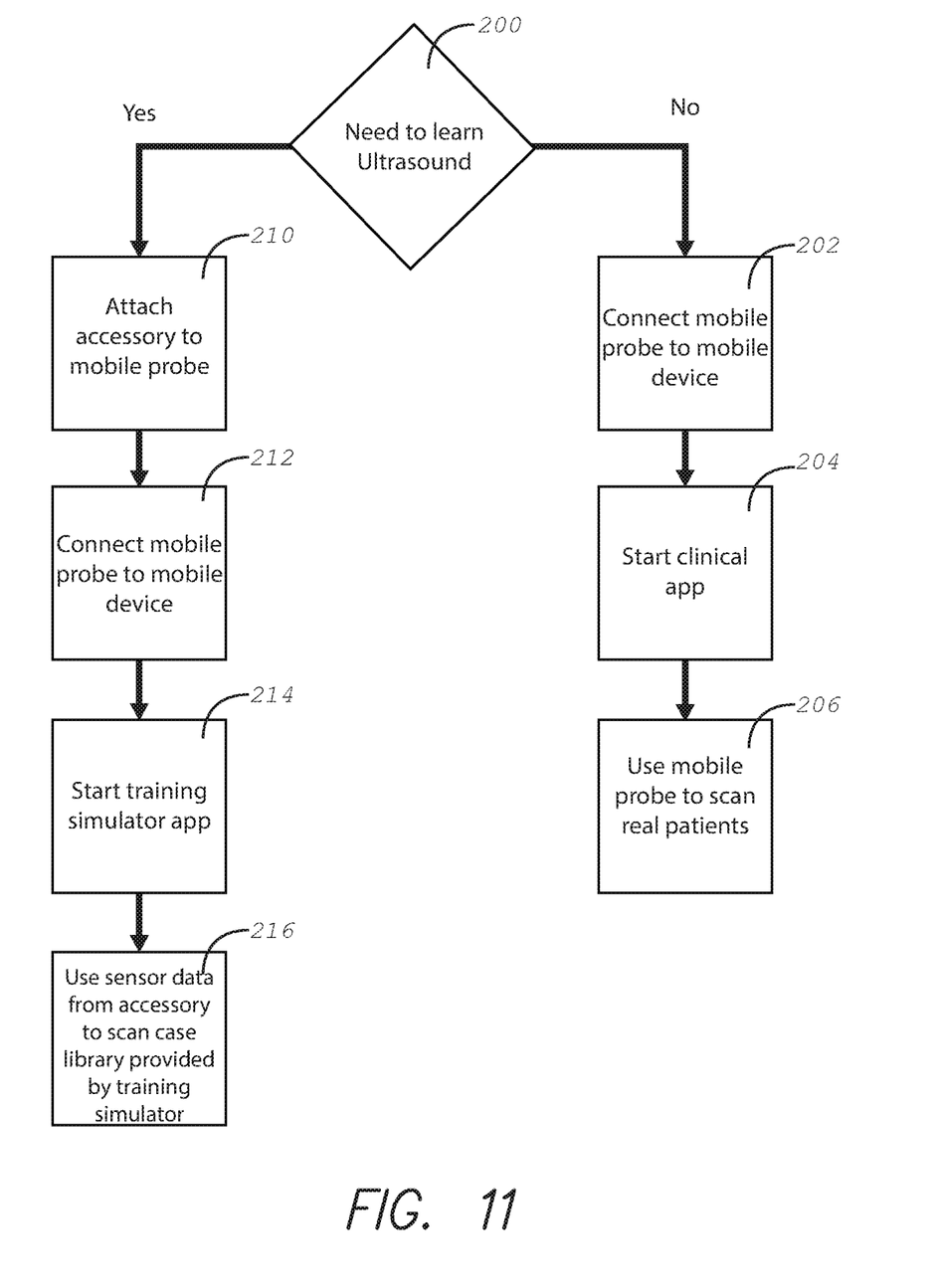
FIG. 11 shows a flow diagram of the use of the present invention.

With reference to FIG. 11, in the preferred embodiment the user must be able to operate the computing device 160 in two distinct modes: a diagnostic mode and a training mode. Therefore, the user must choose 200 between the diagnostic mode and the training mode. In the diagnostic mode, the piezoelectric transducer 114 of the probe 104 must be exposed and the device operates as a traditional imaging device for scanning real patients. The user may prepare the device for diagnostic mode by either ensuring that the motion sensor accessory 150 is removed from the mobile probe 104 or choosing a carrier 152 for the motion accessory 150 that does not interfere with the transducer portion 114 of the mobile probe 104. The user connects 202 the probe 104 to the computing device 160. The user then launches the clinical app 204 that allows the computing device 160 to become an ultrasound machine. The user can then use the probe 104 to scan real patients 206 to perform an actual ultrasound.

In training simulation mode, the user attaches 210 the motion sensor accessory 150 to the probe 104, and connects 212 the probe 104 to the computing device 160. The user can launch a simulator 214, and use the motion sensing capabilities to scan virtual patients 216 loaded in the accompanying simulator app to learn about ultrasound imaging in a simulated environment.

Simulation Software

As shown in FIG. 7, a specifically designed app accompanies the motion sensor accessory 150, or instructions for downloading the app are provided with the motion sensor accessory 150. The app must be designed to provide some or all of the following features: functionality to pair the app with the motion sensor accessory 150, functionality to calibrate the motion sensor accessory 150, a menu or other user interface element 162 to select simulated ultrasound cases from a library, a mode to display a simulated ultrasound image 164 similarly to when the mobile ultrasound probe 104 is used on a real-patient, a mode to display a simulated ultrasound probe 166 alongside a rendering of a virtual body 168 displaying how the ultrasound probe 104 is placed on a patient in the simulated environment.

The suite of software available on the computing device 160 must allow the user to operate the device in either operating mode (diagnostic mode or training mode). Implementers may choose to provide two distinct apps for each mode of operation, requiring the user to manually switch from one to the other, or provide a single app that incorporates functionality to operate the system either in diagnostic ultrasound or training simulation mode.

The foregoing description of the preferred embodiment of the invention has been presented for the purposes of illustration and description. It is not intended to be exhaustive or to limit the invention to the precise form disclosed. Many modifications and variations are possible in light of the above teaching. it is intended that the scope of the invention not be limited by this detailed description, but by the claims and the equivalents to the claims appended hereto.

What is claimed is:

1. A method for using an ultrasound system as a real ultrasound device or a training device, comprising:
    (a) physically connecting a motion sensor accessory to an exterior of an ultrasound probe with a carrier, wherein the motion sensor accessory comprises a motion sensor for detecting position and orientation wherein when the motion sensor accessory is attached to the ultrasound probe, a transducer of the ultrasound probe is covered by the motion sensor accessory and the transducer is automatically turned off by the motion sensor accessory;
    (b) operatively connecting the motion sensor accessory to an ultrasound machine; and
    (c) simulating an ultrasound scan with the ultrasound probe based on a simulation program running on the ultrasound machine, the simulation program selected from a library of pre-recorded ultrasound cases executable by the ultrasound machine to simulate functioning of a real ultrasound scan, wherein when the motion sensor accessory is turned on, the ultrasound probe is inactive for real ultrasound scans.

2. The method of claim 1, wherein when the motion sensor accessory is turned off, the ultrasound probe is active as a diagnostic tool for real ultrasound scans.

3. The method of claim 1, wherein the carrier comprises a harness to attach to the ultrasound probe.

4. The method of claim 1, wherein the ultrasound machine is a mobile device.

5. The method of claim 1, wherein the ultrasound probe comprises a ultrasound circuitry, and wherein the method further comprising using the ultrasound system in a diagnostic mode by:
    (a) turning off the motion sensory accessory;
    (b) activating the ultrasound transducer;
    (c) operating the ultrasound probe to scan a patient, the transducer transmitting acoustic waves and measuring reflected waves to produce a reflected wave signal;
    (d) the ultrasound circuitry receiving the reflected wave signal from the transducer and transmitting an image signal to the ultrasound machine; and
    (e) the ultrasound machine displaying an ultrasound image.

6. The method of claim 1, wherein the step of using the ultrasound system in the training mode further comprises the step of augmenting the library of pre-recorded ultrasound cases with one or more anatomical annotations before navigating the library of pre-recorded ultrasound cases.

7. The method of claim 1, wherein the motion sensor accessory comprises an accessory switch to detect when the motion sensor accessory has been attached to the ultrasound probe.

8. The method of claim 1, wherein the carrier is a cap that covers the transducer, and wherein the step of physically connecting the motion sensor accessory to the exterior of the ultrasound probe comprises covering the transducer at a tip of the ultrasound probe.

9. The method of claim 8, further comprising stretching the carrier over the tip of the ultrasound probe.

\* \* \* \* \*